United States Patent [19]

Cragoe, Jr. et al.

[11] 3,974,212
[45] Aug. 10, 1976

[54] [1-HYDROXIMINO-2,2-DISUBSTITUTED-5-INDANYLOXY-(OR THIO)]ALKANOIC ACIDS

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[22] Filed: May 22, 1974

[21] Appl. No.: 472,262

[52] U.S. Cl. .................. 260/519; 260/247.1 R; 260/247.5 R; 260/293.62; 260/308 D; 260/470; 260/471 R; 260/473 F; 260/501.1; 260/501.21; 260/516; 260/520 C; 260/546; 260/558 S; 260/559 A; 260/590 FA; 424/269; 424/309; 424/315; 424/319
[51] Int. Cl.² .......................................... C07C 131/00
[58] Field of Search ............................. 260/519, 516

[56] References Cited
UNITED STATES PATENTS
3,704,314  11/1972  Cragoe et al. ..................... 260/519

OTHER PUBLICATIONS
Wagner et al., Synthetic Organic Chemistry, John Wiley & Sons, Inc., New York, (1953), pp. 739 and 740.

*Primary Examiner*—Richard L. Raymond
*Attorney, Agent, or Firm*—Michael C. Sudol, Jr.; J. Jerome Behan; Rudolph J. Anderson

[57] ABSTRACT

[1-Hydroximino-2,2-disubstituted-5-indanyloxy-(or thio)]alkanoic acids and their salt, ester, anhydride, amide and 5-tetrazolyl derivatives are disclosed. The products display a dual pharmaceutical utility in that they exhibit diuretic, saluretic and uricosuric activity. The acid products are prepared by treating a 1-oxo-2,2-disubstituted-5-indanyloxy(or thio)alkanoic acids or derivatives thereof with hydroxylamine in the presence of a base.

18 Claims, No Drawings

[1-HYDROXIMINO-2,2-DISUBSTITUTED-5-INDANYLOXY-(OR THIO)]ALKANOIC ACIDS

BACKGROUND OF THE INVENTION

This invention relates to a new class of chemical compounds which can be described generally as 1-hydroximino-2,2-disubstituted-5-indanyloxy(or thio)alkanoic acids and to the non-toxic, pharmacologically acceptable salt, ester, anhydride, amide and 5-tetrazolyl derivatives. It is also an object of this invention to describe a method for the preparation of the 1-hydroximino-2,2-disubstituted-5-indanyloxy alkanoic acids. Pharmacological studies show that the instant products are effective diuretic and saluretic agents which can be used in the treatment of conditions associated with electrolyte and fluid retention. The instant products are also useful in the treatment of hypertension. In addition, these compounds are able to maintain the uric acid concentration in the body at pretreatment levels or to even effect a decrease in the uric acid concentration. All of the compounds of this invention possess the described utilities; however, by structural modifications various ratios of these activities are observed.

When administered in therapeutic dosages, in conventional vehicles, the instant products effectively reduce the amount of sodium and chloride ions in the body, lower dangerous excesses of fluid levels to acceptable levels and, in general, alleviate conditions usually associated with edema. In addition, these compounds overcome a major problem associated with many of the presently available diuretics and saluretics. Many of the presently available diuretics and saluretics have a tendency upon administration to induce hyperuricemia which may precipitate uric acid or sodium urate, or both, in the body which may cause from mild to severe cases of gout. The instant compounds of this invention now provide an effective tool to treat those patients (both human and animal) requiring diuretic and saluretic treatment without incurring the risk of inducing gout.

Thus, it is an object of the present invention to provide 1-hydroximino-2,2-disubstituted indanes of the above general description and to provide processes for the preparation thereof.

A further object of this invention is to provide pharmaceutical compositions comprising therapeutically effective amounts of such 1-hydroximino-2,2-disubstituted indanes and to provide a method of treatment comprising administering such compounds and compositions.

DETAILED DESCRIPTION OF THE INVENTION

The [1-hydroximino-2,2-disbustituted-5-indanyloxy-(or thio)]alkanoic acids (I) of the invention have the following structural formula:

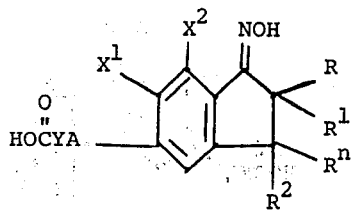

I wherein A is oxygen or sulfur; R is lower alkyl containing from 1 to 5 carbon atoms such as methyl, ethyl, n-propyl, isopropyl, n-butyl, isobutyl, tert-butyl, n-pentyl and the like; cycloalkyl, for example, cycloalkyl containing from 3-6 nuclear carbon atoms such as cyclopropyl, cyclobutyl, cyclopentyl, cyclohexyl; phenyl, and halo-, hydroxy-, nitro-, lower alkoxy-, and lower alkyl-substituted phenyl and the like; $R^1$ is lower alkyl containing from 1 to 5 carbon atoms such as methyl, ethyl, n-propyl, isopropyl, n-butyl, isobutyl, tert-butyl, n-pentyl and the like, lower alkenyl containing from 3 to 5 carbon atoms such as allyl, 1-, 2- or 3-butenyl, 1-, 2-, 3- or 4-pentenyl and the like; lower alkynyl containing from 3 to 5 carbon atoms such as propargyl, 1-, 2- or 3-butynyl, 1-, 2-, 3- or 4-pentynyl and the like, phenyl lower alkyl wherein the the lower alkyl contains from 1 to 3 carbon atoms such as benzyl, phenethyl, phenylpropyl and the like, phenyl lower alkenyl such as cinnamyl and the like, hydroxy lower alkyl, for example, hydroxymethyl and the like, hydroxycycloalkyl, for example, hydroxycyclopentyl or hydroxycyclohexyl, cycloalkyl lower alkyl containing 4 to 7 carbon atoms, for example, cyclopropylmethyl, cyclopentylmethyl and the like; lower alkoxy lower alkyl, oxo lower alkyl and the like; or R and $R^1$ may be joined together with the carbon atoms to which they are attached to form a cycloalkyl radical containing from 3 to 7 nuclear carbon atoms which may be unsubstituted or lower alkyl- or hydroxy-substituted, for example, cyclopropyl, cyclobutyl, cyclopentyl, cyclohexyl, cycloheptyl, methylcyclopropyl, hydroxy-cyclopentyl, and the like; $R^2$ is hydrogen, lower alkyl containing from 1-5 carbon atoms, or aryl such as phenyl or substituted aryl wherein the substituent is lower alkyl; $R^1$ and $R^2$ may be joined together to form a hydrocarbylene ring; $R^n$ is hydrogen or methyl; $X^1$ is hydrogen, methyl or halo such as chloro, bromo, fluoro and the like and $X^2$ is methyl or halo such as chloro, bromo, fluoro and the like or $X^1$ and $X^2$ may be joined to form a hydrocarbylene chain containing from 3 to 4 carbon atoms, for example, trimethylene, tetramethylene, 1,3-butadienylene and the like; and Y is an alkylene or haloalkylene radical having from 1 to about 4 carbon atoms for example, methylene, ethylidene, propylidene, isopropylidene, ethylene, trimethylene, fluoromethylene and the like. The invention also includes the pharmaceutically acceptable salt, the ester, anhydride and amide derivatives and the derivatives wherein a 5-tetrazolyl radical replaces the carboxy group.

A preferred embodiment of this invention comprises compounds of Formula I above wherein A is oxygen Y is —$CH_2$—, $X^1$, $X^2$, R, $R^1$, $R^2$ and $R^n$ are as above defined and the non-toxic pharmaceutically acceptable salts thereof.

More preferred embodiments of this invention are the (1-hydroximino-2,2-disubstituted-6,7-disubstituted-5-indanyloxy)acetic acids having the following structural formula:

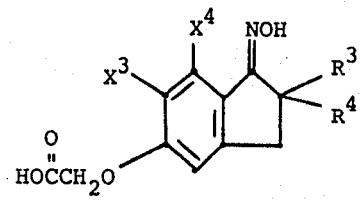

Ia wherein $R^3$ is phenyl or halo-, hydroxy-, lower alkyl or lower alkoxy-substituted phenyl, or lower alkyl containing from 1–3 carbon atoms; cycloalkyl containing 5 to 6 nuclear carbon atoms such as cyclopentyl or cyclohexyl; hydroxy cycloalkyl containing 4 to 6 carbon atoms such as hydroxycyclopentyl or hydroxycyclohexyl; or phenyl loweralkyl such as benzyl; $R^4$ is lower alkyl containing from 1 to 3 carbon atoms such as methyl, ethyl, n-propyl or isopropyl; or $R^3$ and $R^4$ may be joined together with the carbon atom to which they are attached to form a cycloalkyl radical containing from 5 to 6 nuclear carbon atoms such as cyclopentyl, cyclohexyl and the like; and $X^3$ and $X^4$ are the same or different radicals selected from methyl or chloro and the non-toxic, pharmacologically acceptable salt derivatives. The foregoing class of compounds exhibits particularly good diuretic and saluretic activity and also either maintains the uric acid concentration in the body at pretreatment levels or even causes a decrease in the uric acid concenttration.

The 1-hydroximino compounds of this invention (I) are most conveniently prepared by reacting a 1-oxo-2,2-disubstituted-5-indanyloxy(or thio)alkanoic acid (Ib) with hydroxylamine in the presence of a base. There is no criticality as to the identity of the base which may be, for example, pyridine, or an alkali metal or alkaline earth metal oxide or hydrous oxide such as potassium hydroxide or sodium hydroxide. There is no criticality as to the identity of the solvent system; the sole requirement being that the reactants be reasonably soluble therein and substantially inert to avoid unwanted side reactions. Suitable solvents are water, ethanol, 2-propanol, pyridine, and the like. The reaction, depicted below, is preferably conducted at the reflux temperature of the particular solvent employed and requires from about 2 to about 48 hrs.

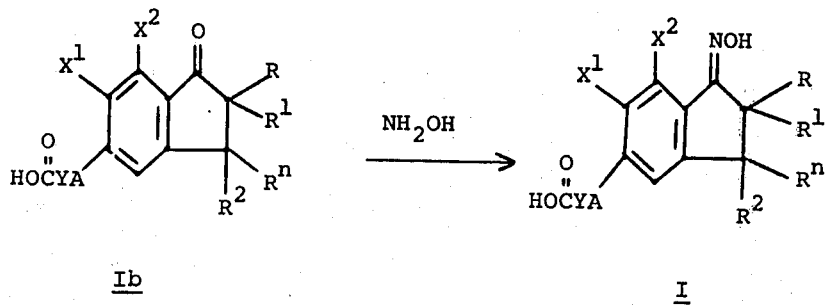

The precursor 1-oxo-2,2-disubstituted-5-indanyloxy-(or thio)alkanoic acids (Ib), which also exhibit diuretic, saluretic and uricosuric activity, may be prepared by an etherification method which comprises reacting a halo alkanoic acid or ester thereof of the formula:

wherein $R^5$ is hydrogen or lower alkyl such as methyl, ethyl and the like and Z is halo such as bromo, chloro, iodo and the like with a suitable 2,2-disubstituted-5-hydroxy-(or mercapto)-1-indanone (II, infra). The following equation illustrates this reaction:

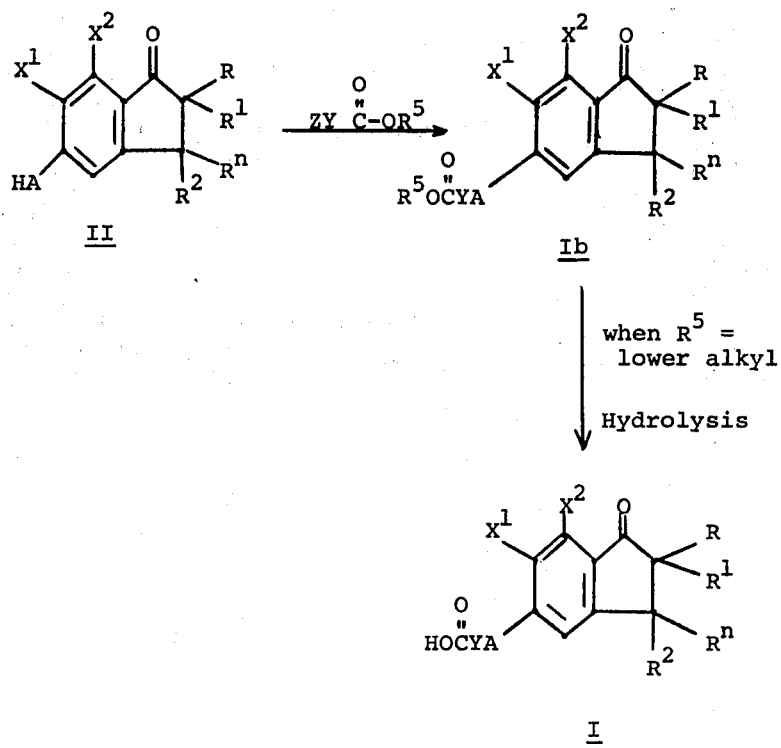

wherein all substituents are as defined above.

In general, the reaction is conducted in the presence of a base such as an alkali metal carbonate, hydroxide or alkoxide such as potassium carbonate, sodium carbonate, potoassium hydroxide, sodium hydroxide, sodium ethoxide, and the like. Any solvent which is inert or substantially inert to the reactants and in which the reagents are reasonably soluble may be employed. Acetone, ethanol and dimethylformamide, for example, have proved to be particularly advantageous solvents. The reaction may be conducted at a temperature in the range of from about 25°C. to the reflux temperature of the particular solvent employed. The reaction with the halo alkanoic acid or ester is generally complete in about 10 to 60 minutes. If the halo alkanoic acid ester is employed, the ester obtained may be hydrolyzed to the free acid by methods well known to those skilled in the art.

Those [1-oxo-2,2-disubstituted-5-indanyloxy(or thio)]alkanoic acids (Ib) wherein the alkylene chain contains 2-linear carbon atoms between the carboxy and oxy (or thio) groups are prepared from their corresponding 2,2-disubstituted-5-hydroxy(or mercapto)-1-indanones (II) by the reaction of the latter with propiolactone or with an appropriately substituted propiolactone, in the presence of a base such as an aqueous solution of sodium hydroxide, preferably, while heating the solution at reflux temperatures; followed by the acidification of the carboxylate intermediate thus formed to the desired acid. The following equation illustrates the reaction:

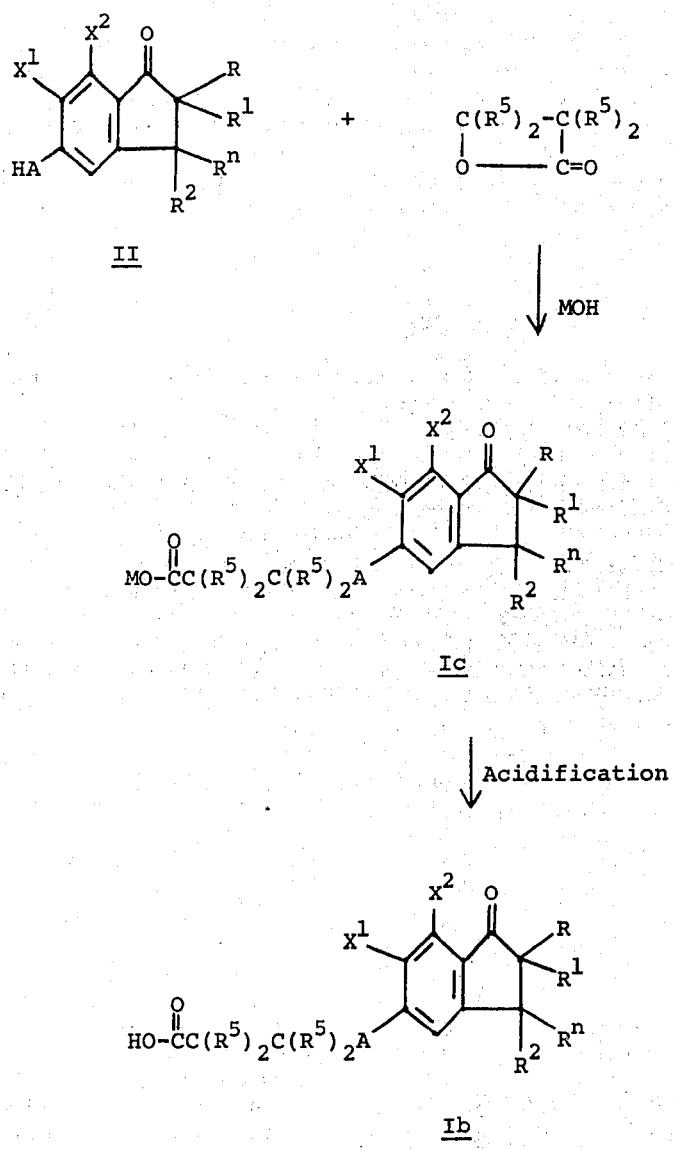

wherein all substituents are as defined above and M is a cation derived from an alkali metal hydroxide or alkali metal carbonate such as a sodium or potassium cation.

The 2,2-disubstituted-5-hydroxy-(or mercapto)-1-indanones (II, infra), are prepared by treating the correspondingly substituted 2,2-disubstituted-5-lower alkoxy(or lower alkylthio)-1-indanone with an ether cleaving reagent such as aluminum chloride, pyridine hydrochloride, sodium in liquid ammonia and the like. When aluminum chloride is employed, the solvent may be heptane, carbon disulfide, methylene chloride and the like and when pyridine hydrochloride is employed, it is not necessary to employ a solvent. The following equation illustrates this process:

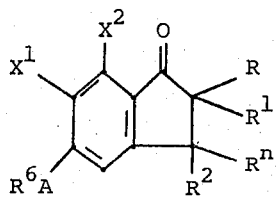

III

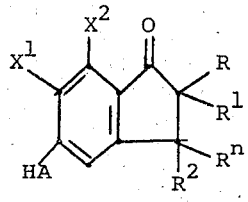

II ether cleavage wherein A, R, $R^1$, $R^2$, $R^n$, $X^1$ and $X^2$ are as defined above, and $R^6$ is lower alkyl.

The 2,2-disubstituted-5-lower alkoxy (or lower alkyl thio)-1-indanones (III, supra) are prepared by treating a 2-substituted-5-lower alkoxy-(or lower alkyl thio)-1-indanone (IV, infra) with a suitable alkylating or aylating reagent of the formula: $R^1Z$ and

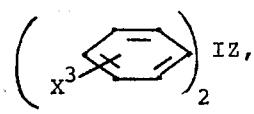

respectively, wherein $R^1$, $X^3$ and Z are defined above. This reaction is conducted by first treating the 2-substituted-5-lower alkoxy-1-indanone (IV) with a suitable base, for example, an alkali metal hydride such as sodium hydride and the like, or an alkali metal alkoxide, for example, potassium tertiary butoxide and the like. Other bases which may be employed include sodium amide, lithium amide and the like. This resulting carbanion is then treated with either the alkylating reagent, or the arylating reagent. Any solvent which is inert or substantially inert to the reactants employed may be used. Suitable solvents include, for example, 1,2-dimethoxyethane, tertiary butanol, benzene, dimethylformamide and the like. The reaction may be conducted at a temperature in the range of from about 25° to about 150°C. In general, the reaction is conducted at a temperature in the range of from about 75° to about 90°C.

The following equation illustrates this process:

The 2-substituted-5-lower alkoxy (and lower alkyl thio)-1-indanones (IV, supra) employed above may be prepared by several routes. One route comprises treating the 2-substituted-5-hydroxy-1-indanone with an alkylating agent such as dimethylsulfate or diethylsulfate in the presence of a base such as sodium hydroxide or potassium hydroxide. Other alkylating agents which may be employed include methyl iodide, ethyl iodide and the like employing dimethylformamide as the preferred solvent and as the base, potassium carbonate. The 2-substituted-5-hydroxy-(and 5-mercapto)-1-indanones employed in this particular procedure are known compounds described in U.S. Pat. No. 3,668,241.

A second method for preparing the 2-substituted-5-lower alkoxy-(and lower alkyl thio)-1-indanones (IV) comprises the cyclialkylation of a nuclear lower alkoxy (or lower alkyl thio) substituted [2-alkylidenealkanoyl (or 2-alkylidene aralkanoyl)]benzene (V, infra) by treatment with an electron-acceptor acid, for example, a Lewis acid such as concentrated sulfuric acid, polyphosphoric acid, boron trifluoride and the like. The reaction may be conducted at a temperature in the range of from about 0° to about 60°C., in general, the reaction is conducted at ambient temperature.

The following equation illustrates this process:

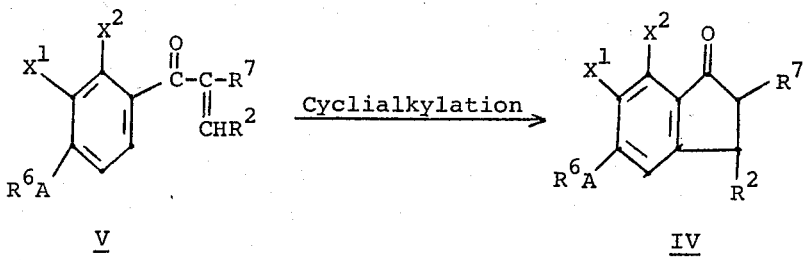

V                    IV wherein all substituents are as defined above and $R^7$ is R or $R^1$.

The 2-spiro-5-lower alkoxy-(and lower alkyl thio)-1-indanones (IVa) are prepared by treating a 2-($\alpha$-haloalkyl)-5-lower alkoxy-(or lower alkylthio)-1-indanone (IVb) with a base, for example, an alkali metal hydride such as sodium hydride and the like in a suitable inert solvent such as 1,2-dimethoxyethane at the reflux temperature of the particular solvent employed.

The following equation illustrates this process:

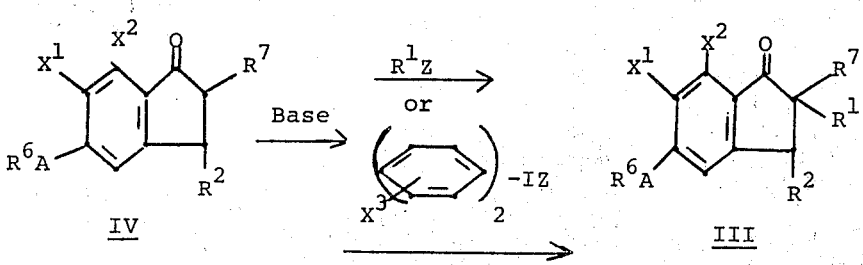

IV                    III wherein all substituents are as defined above, and $R^7$ is R or $R^1$ when the reaction involves alkylation or arylation respectively.

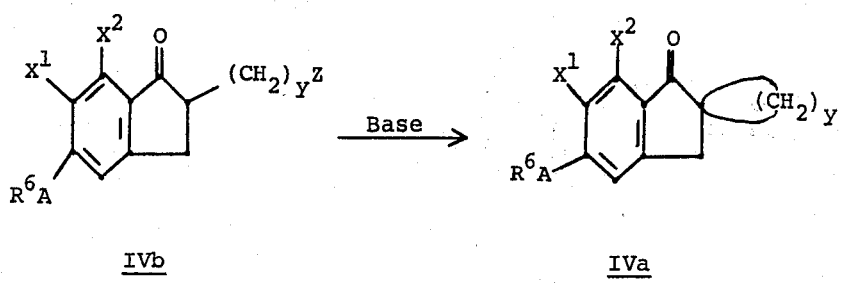

IVb            IVa wherein A, $R^6$, $X^1$, $X^2$ and Z are as defined above and y is an integer having a value of from 3 to 6.

The nuclear lower alkoxy (and lower alkyl thio) (2-alkylidenealkanoyl)benzenes (V, supra) employed above may be prepared by alternate methods. One method, limited to the preparation of the nuclear lower alkoxy-(or lower alkyl thio)-4-(2-methylenealkanoyl)-benzenes (Va), comprises treating a nuclear lower alkoxy-(or lower alkyl thio)-4-alkanoylbenzene (VI) with dimethylamine hydrochloride and paraformaldehyde followed by treatment of the Mannich intermediate (VIa), thus obtained, with aqueous sodium bicarbonate or anhydrous dimethylformamide, either with or without heat, to afford the desired compound, Va. The following equation illustrates this process:

dehydrobrominating agent such as lithium bromide, lithium chloride and the like. Suitable solvents for this reaction include dimethylformamide and the like. This reaction is conveniently conducted at a temperature in the range of from about 50° to about 120°C. for a period of time of from about one hour to about six hours. The following equation illustrates this reaction.

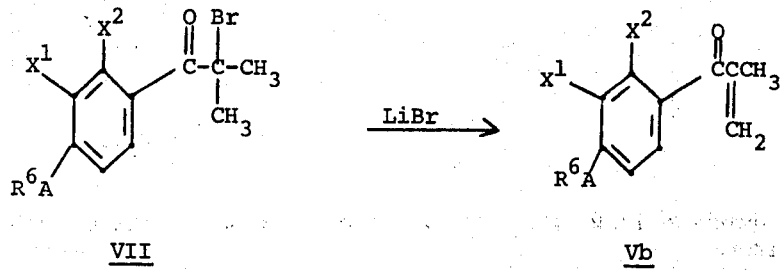

VII            Vb wherein A, $R^6$, $X^1$ and $X^2$ are as defined above.

A third method for preparing the compounds of formula V and one for the preparation of the homologous 4-(2-alkylidenealkanoyl)benzenes (Vc), for example, the 4-(2-ethylidene) and 4-(2-propylidene) homologs, comprises treating a nuclear lower alkoxy (or lower alkylthio) substituted benzene (IX, infra) with an appropriate branched chain alkanoyl halide such as 2-

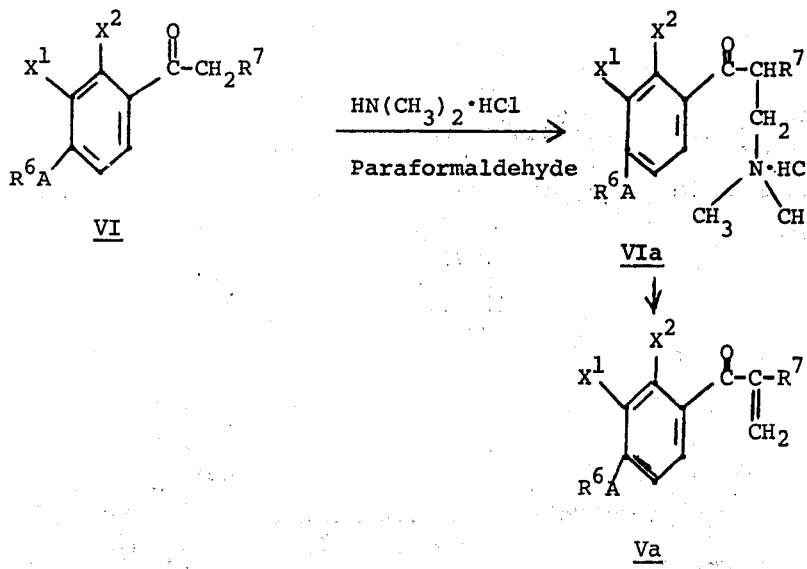

VI

VIa

↓

Va wherein A, $R^6$, $R^7$, $X^1$ and $X^2$ are as defined above.

A second method for preparing the nuclear lower alkoxy-(and lower alkyl thio)-2-(alkylidenealkanoyl)-benzenes (Vb) and one limited to preparing those compounds wherein $R^7$ is methyl, comprises treating anuclear lower alkoxy-(or lower alkyl thio) substituted 2-bromo-2-methylpropionylbenzene (VII, infra) with a methylbutyryl chloride, 2-ethylbutyryl chloride and the like in the presence of a Friedel-Crafts catalyst to afford the corresponding [4-nuclear lower alkoxy (or lower alkyl thio) substituted] alkanoylbenzene (VIIa); which is halogenated and then dehydrohalogenated to afford the 4-(2-alkylidenealkanoyl)-benzene (Vc). The following equation illustrates this process:

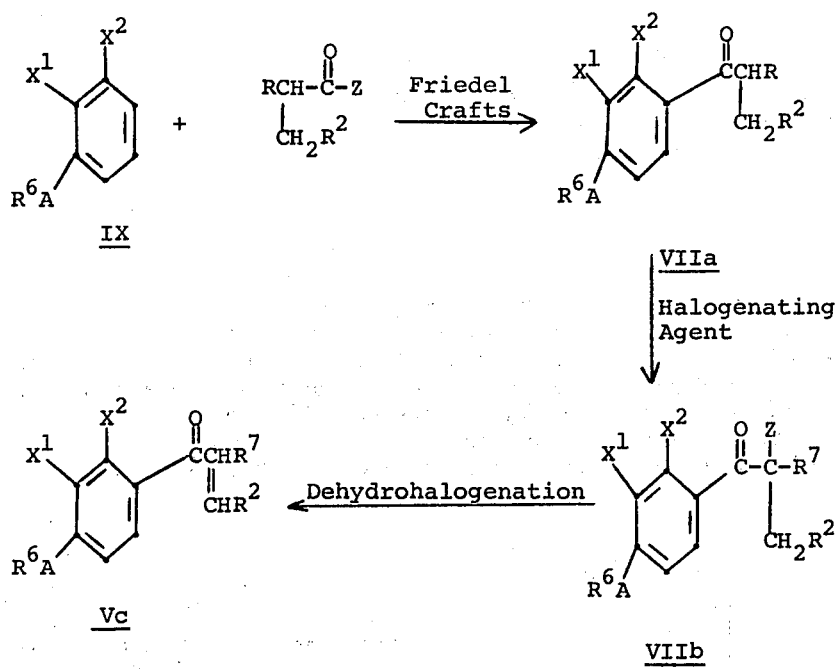

wherein A, $R^7$, $R^2$, $R^6$, $X^1$, $X^2$ and Z are as defined above.

A fourth method for preparing compounds of Formula V, and one for the preparation of those compounds wherein $R^2$ in Formula I is phenyl comprises treating a nuclear lower alkoxy(or alkylthio)-4-alkanoyl benzene (VIII) with benzaldehyde in a suitable solvent such as water, dimethylsulfoxide and the like in the presence of a base such as sodium hydroxide, potassium hydroxide, either with or without heat, to afford the desired compound V$d$. The following equation illustrates this process:

A fifth method for preparing compounds of Formula V wherein $R^2$ is hydrogen, comprises treating a 4-lower alkoxy (or lower alkyl thio) or alkanoyl or aralkanoyl benzene (VIII) with a methylene inserting reagent such as a bis-dimethylaminomethane in the presence of an alkanoic acid anhydride such as acetic anhydride. The reaction is conducted at a temperature of from about 25° to about 100°C. Any solvent which is inert of substantially inert to the reactants employed may be used, but in general the methylene inseting reagent, such as bis-dimethylaminomethane, serves as the solvent medium. The following equation illustrates this process:

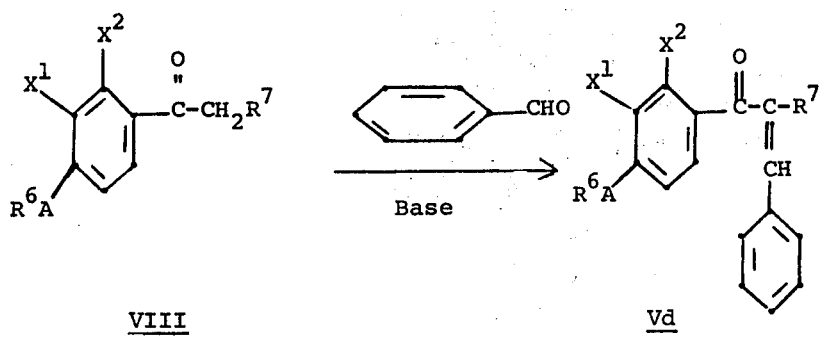

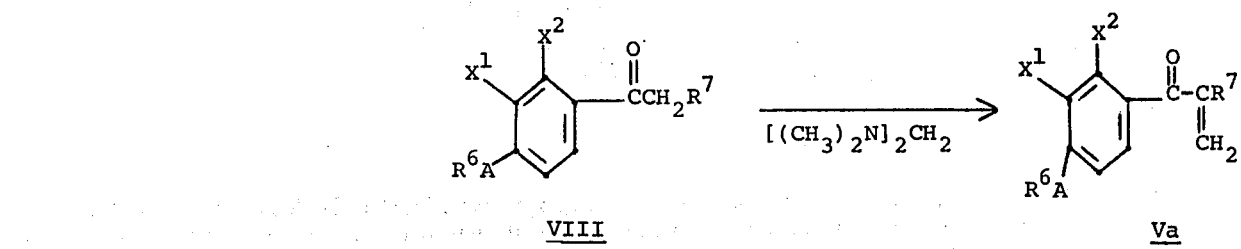

wherein A, $R^7$, $R^6$, $X^1$ and $X^2$ are as defined above.

wherein all substituents are as defined above.

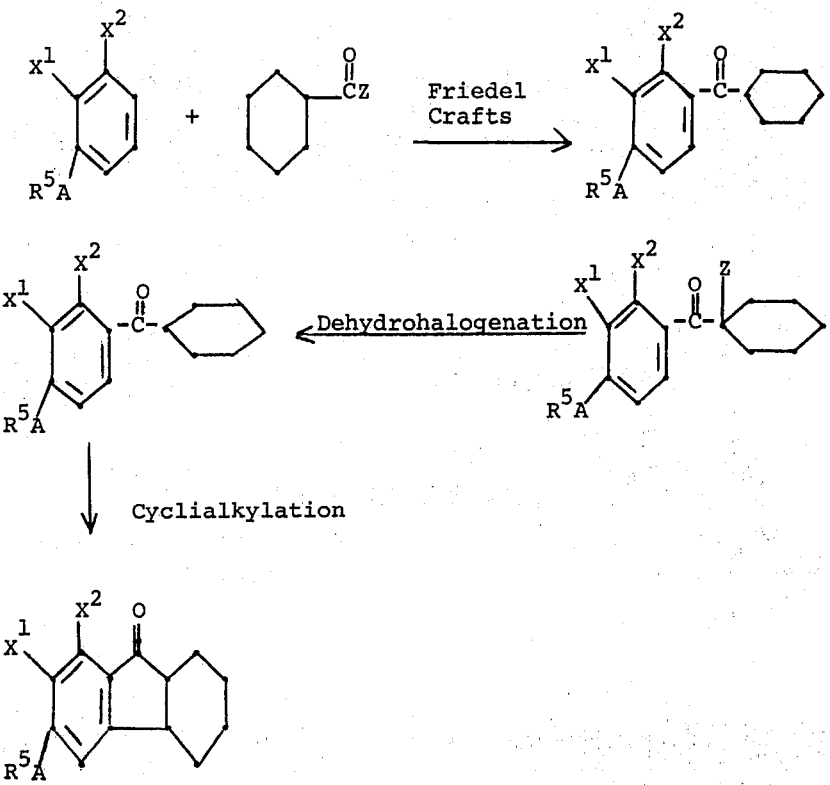

The [4-nuclear lower alkoxy (and lower alkyl thio)-substituted]alkanoyl benzenes (VIII) are either known compounds or may be prepared by the reaction of an alkanoyl halide with a nuclear lower alkoxy (or lower alkyl thio) substituted benzene (IX, infra) in the presence of a Friedel-Crafts catalyst such as aluminum chloride and the like. The reaction solvent and the temperature at which the reaction is conducted are not particularly critical aspects of this reaction inasmuch as any solvent which is inert to the acyl halide and nuclear lower alkoxy (or lower alkyl thio) substituted benzenes may be employed with good results. In this regard, it has been found that methylene chloride is a particularly suitable solvent. The following equation illustrates this reaction:

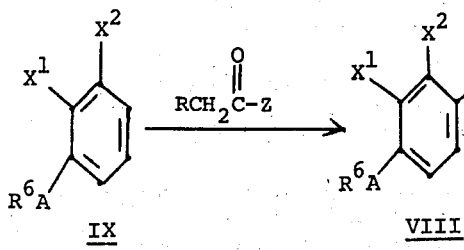

wherein A, R, $R^7$, $X^1$, $X^2$ and Z are as defined above.

The nuclear lower alkoxy precursors of those compounds of the instant invention wherein $R^1$ and $R^2$ are joined to form a hydrocarbylene ring are prepared according to the procedure described in copending commonly assigned application Ser. No. 399,568, filed Sept. 21, 1973 (Merck & Co., Inc. attorney's docket No. 15584 entitled [1-Oxo-2,3-Hydrocarbylene-5-Indanyloxy(or Thio)]Alkanoic Acids; Edward J. Cragoe, Jr. and Otto W. Woltersdrof, Jr. which application is incorporated herein by reference. The following sequence illustrates their process wherein $R^1$ and $R^2$ are joined to form a cyclohexylene ring:

wherein the substituents are as defined above.

Those indanyloxyalkanoic acids wherein R and $R^1$ are joined to form a cyclopropyl or lower alkyl cyclopropyl may be prepared by treating the correspondingly substituted 2-alkylideneindanyloxyalkanoic acids with an alkali metal base such as sodium hydride and the like followed by treatment with a methylating agent, for example, trimethylsulfoxonium iodide and the like. The preparation of the 1-oxo-2-alkylideneindanyloxyalkanoic acids is described in U.S. Pat. No. 3,704,317. The following equation illustrates this reaction:

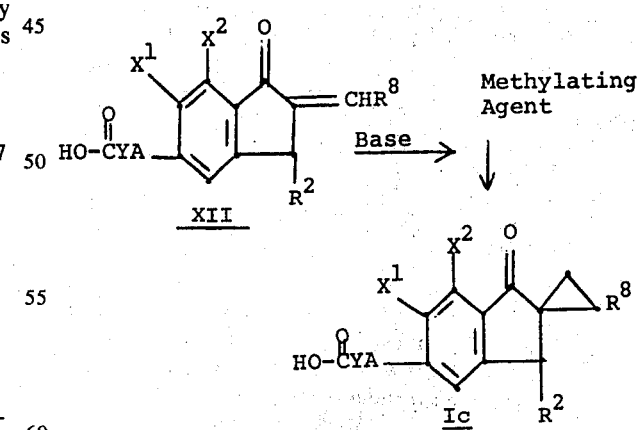

wherein all substituents are as defined above and $R^8$ is hydrogen or loweralkyl of from 1 to 4 carbon atoms or cycloalkyl.

The 1-oxo-2,2-disbustituted-5-indanyloxyalkanoic acids, wherein $R^1$ is hydroxy lower alkyl, are prepared by treating a 1-oxo-2-substituted-5-indanyloxyalkanoic acid (XIV) with formaldehyde in the presence of a base such as sodium hydroxide and the like, followed by acidification to afford the desired acid. The following equation illustrates this process:

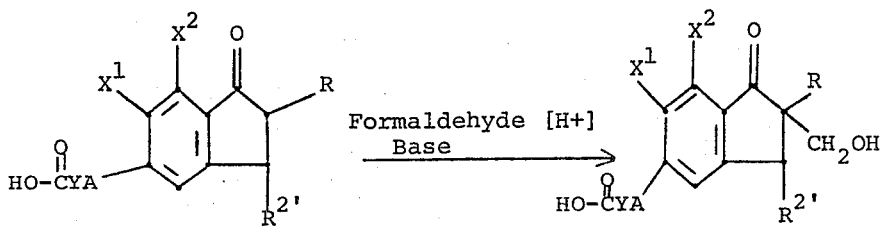

XIV          Ie wherein all substituents are as defined above. The 1-oxo-2-substituted-5-indanyloxyalkanoic acids are described in Great Britain Pat. No. 1,254,908.

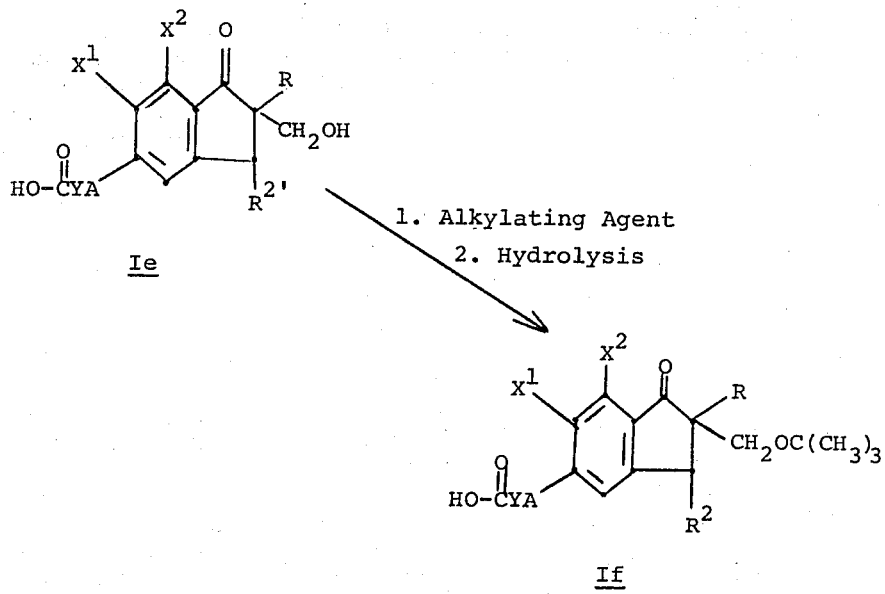

Another method is to treat a 1-oxo-2-substituted-5-indanyloxyalkanoic acid with sodium alkoxide and methyl vinyl ketone in an inert atmosphere and then reducing the oxoalkyl substituent to a hydroxy alkyl with a reducing agent such as potassium borohydride.

The 1-oxo-2,2-disubstituted-5-indanyloxyalkanoic acids wherein $R^1$ is hydroxycycloalkyl are prepared generally by biological means. For example, to a typical cultured medium one can add a small amount of microorganism as a starter and after about 48 hours of culturing this broth medium compound of Formula I can then be added to the cultured medium. After a sufficient time for conversion, generally about 48 hours, the 1-oxo-2-(hydroxycycloalkyl)indanyloxyalkanoic acid can be extracted by acidifying the media and isolating the hydroxylated product along with some starting material in an organic solvent, generally a solvent which produces a 2 phase system. The 1-oxo-2-(hydroxycycloalkyl)indanyloxyalkanoic acid can then be separated from the starting material by thin layer chromatography. The culture medium can be any typical culture medium known to those skilled in the art whereas the microorganism which performs the conversion should generally be a fungal type rather than a bacterial type.

The 1-oxo-2,2-disubstituted-5-indanyloxyalkanoic acids wherein $R^1$ is alkoxyalkyl (If, infra) may be prepared by treating a correspondingly substituted hydroxyalkylindanyloxyalkanoic acid (Ie, supra) with a suitable alkylating agent such as isobutylene and the like followed by hydrolysis of the resultant ester. The following equation illustrates this process:

wherein R, $R^2$, $X^1$, $X^2$, A and Y are as above-defined.

As previously mentioned, the non-toxic, pharmacologically acceptable salts of the 1-hydroximino-2,2-disubstituted-5-indanyloxy(or thio)alkanoic acids (I) are within the scope of this invention and are prepared by conventional methods well known in the art. Thus, the acid upon reaction with alkali metal and alkaline earth metal hydroxides, carbonates, bicarbonates, amines or quaternary ammonium hydroxides, forms the corresponding alkali metal, alkaline earth metal, amino or quaternary ammonium salt. These salts are particularly useful as parenteral solutions because they are very soluble in pharmaceutical carriers such as water or alcohol.

The anhydride derived from the carboxylic acids for Formula I are included in the invention.

Also included within the scope of this invention are the ester and amide derivatives of the instant products which are prepared by conventional methods well known to those skilled in the art. Thus, for example, the ester derivative may be prepared by the reaction of a 1-hydroximino-2,2-disubstituted-5-indanyloxy(or thio)alkanoic acid of this invention with an alcohol, for example, with a lower alkanol. The amide derivatives may be prepared by converting a 1-hydroximino-2,2-disubstituted-5-indanyloxy (or thio)alkanoic acid to its corresponding acid chloride by treatment with thionyl chloride followed by treating said acid chloride with ammonia, an appropriate mono-lower alkyl amine, di-lower alkyl amine or a hetero amine, such as piperidine, morpholine and the like, to produce the corresponding amide compound. Included also are the N-amidino derivatives of the amides particularly the N-amidino indanyloxyacetamide derivative of the compounds of Formula I. These and other equivalent methods for the preparation of the ester and amide derivatives of the instant products will be apparent to one having ordinary skill in the art and to the extent that said derivatives are both non-toxic and physiologically acceptable to the body system, said derivatives are the functional equivalent of the corresponding 1-hydroxyimino-2,2-disubstituted-5-indanyloxy(or thiol)alkanoic acids.

In addition to the salts, esters, anhydrides and amides being functionally equivalent to the carboxylic products, those compounds wherein the carboxylic acid is replaced by a 5-tetrazolyl radical are also functionally equivalent to the carboxylic acids. These tetrazole analogs (I$h$) are prepared as depicted in the following equation:

hydroximino-2,2-disubstituted-5-indanyloxy(or thio)-]alkanoic acids (I) of this invention.

Many of the instant compounds (I) herein disclosed contain an asymmetric carbon atom in the 2-position of the indanyl ring, i.e., alpha to the carbonyl groups. When this situation exists, the optical antipodes may be separated by methods described below. This invention embraces, therefore, not only the racemic [1-hydroximino-2,2-disubstituted-5-indanyloxy(or thio)]alkanoic acids but also their optically active antipodes.

Separation of the optical isomers of the racemic acids (I) may be accomplished by forming a salt of the racemic mixture with an optically active base such as (+) or (−) amphetimine, (−)-cinchonidine, dehydroabietylamine, (+) or (−)-α-methylbenzylamine, (+) or (−)-α-(1-naphthyl)-ethylamine, brucine or strychnine and the like in a suitable solvent such as methanol, ethanol, 2-propanol, benzene, acetonitrile, nitromethane, acetone and the like. There is thus formed in the solution two diastereomeric salts one of which is usually more soluble in the solvent than the other. Repetitive recrystallization of the crystalline salt generally affords a pure

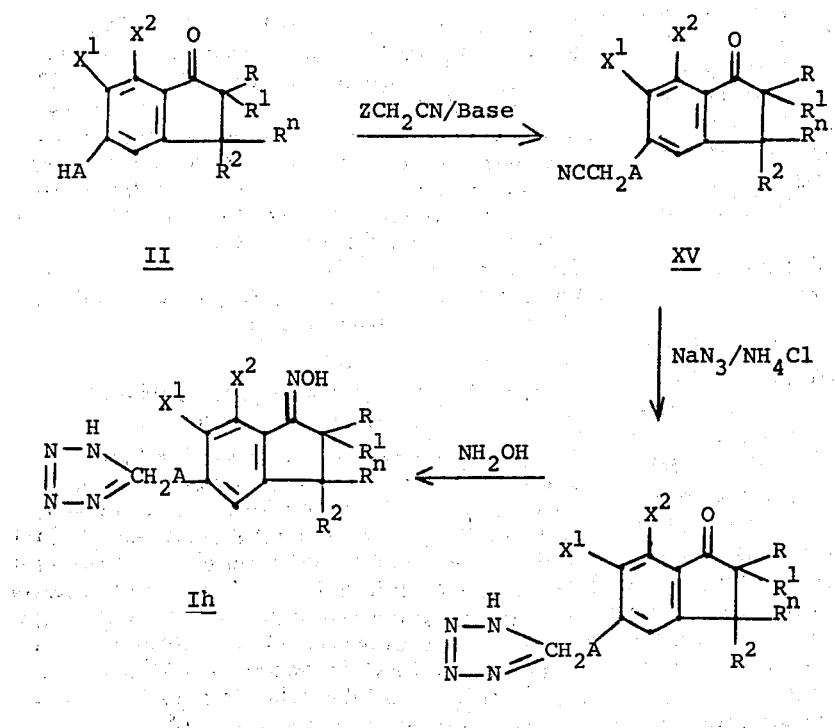

wherein all substituents and Z are as defined above.

The 2,2-disubstituted-5-hydroxy-1-indanone (II) is treated with a haloacetonitrile such as chloroacetonitrile, bromoacetonitrile or iodoacetonitrile in the presence of a base such as potassium carbonate and the like in a suitable solvent such as acetone, dimethylformamide, dimethoxyethane and the like at a temperature in the range of from 25° to 100°C. to afford the corresponding nitrile (XIV, supra) which, upon treatment with sodium azide and ammonium chloride in dimethylformamide at a temperature in the range of from 25° to 100°C., affords the 5-(1-oxo-2,2-disubstituted-5-indanyloxymethyl)tetrazole (I$g$, supra). The tetrazole analogue (I$h$) is obtained by treating I$g$ with hydroxylamine in the presence of a base in a manner exactly as previously described for the preparation of the [1- diastereomer. The optically pure 1-hydroximino-2,2-disubstituted-5-indanyloxy(or thio) alkanoic acid is obtained by acidification of the salt with a mineral acid, extraction into ether, evaporation of the solvent and recrystallization of the optically pure antipode. The other optically pure antipode may generally be obtained by using a different base to form the diastereomeric salt. It is of advantage to isolate the partially resolved acid from the filtrates of the purification of the one diastereomeric salt and to further purify this substance through the use of another optically active base.

The examples which follow illustrate the [1-hydroximino-2,2-disubstituted-5-indanyloxy(or thio)]-alkanoic acid products (I) of the invention and the methods by which they are prepared. However, the examples are illustrative only and it will be apparent to those having ordinary skill in the art that all of the products embraced by formula I, supra, may also be prepared in an analogous manner by substituting the appropriate starting materials for those set forth in the examples.

EXAMPLE 1

(1-Hydroxyimino-2-cyclopentyl-2-methyl-6,7-dichloro-5-indanyloxy)-acetic acid

Step A:
2',3'-Dichloro-4'-methoxy-2-cyclopentylacetophenone 2,3-Dichloroanisole (57.8 g., 0.327 mole) is dissolved in dichloromethane (300 ml.) and cyclopentylacetyl chloride (52.7 g., 0.367 mole) is added. The solution is cooled to +5°C. and aluminum chloride (48.0 g., 0.36 mole) is added gradually over a hour period at +5°C. The mixture is stirred for 2 hours at +5°C. and at 20°–25°C. for 16 hours and then poured into 1 l. of ice water containing 150 ml. of 12N hydrochloric acid. The organic phase is separated and the aqueous phase is extracted with dichloromethane. The combined organic phases are washed with sodium chloride solution, 10% sodium hydroxide and again with sodium chloride solution and dried over magnesium sulfate. On evaporation of the solvent a brown solid is obtained which is crystallized from hexane to obtain 53.2 g. of 2', 3'-dichloro-4'-methoxy-2-cyclopentylacetophenone, m.p. 60°–61.5°C.

Elemental analysis for $C_{15}H_{16}Cl_2O_2$: Calc.: C, 58.55; H, 5.62; Found: C, 58.72; H, 5.71.

Step B: 2,3-Dichloro-4-(2-cyclopentylacryloyl)-anisole

2',3'-Dichloro-4'-methoxy-2-cyclopentyl-acetophenone (51.6 g., 0.18 mole) is dissolved in dioxane (460 ml.) and paraformaldehyde (21.6 g., 0.72 mole) and concentrated sulfuric acid (9.65 g.) are added. The mixture is heated at 80°–85°C. for 20 hours. The dioxane is evaporated at reduced pressure. Water is added to the residual gum which then is extracted into ether. The ether extract is washed with water and dried over magnesium sulfate. The ether is evaporated and upon triturating the residue with hexane (5 ml.) there is obtained a solid that is crystallized from ligroin to obtain (33.3 g.), m.p. 59°–63°C. Crystallization from butyl chloride affords a sample (m.p. 66°–67.5°C.) for analysis.

Elemental analysis for $C_{16}H_{16}Cl_2O_2$: Calc.: C, 60.21; H, 5.37; Found: C, 60.19; H, 5.42.

Step C:
2-Cyclopentyl-5-methoxy-6,7-dichloro-1-indanone 2,3-Dichloro-4-(2-cyclopentyacryloyl)-anisole (33.3 g.) is dissolved in 98% sulfuric acid (150 ml.) and stirred at 20°C. for 1.5 hours. The solution then is added dropwise with stirring to ice water. The aqueous phase is decanted from the gummy product and fresh water is added. After 20 hours the gum solidifies and is crystallized from hexane-benzene (3:1) to obtain 2-cyclopentyl-5-methoxy-6,7-dichloro-1-indanone, m.p. 116°–117°C.

Elemental analysis for $C_{16}H_{16}Cl_2O_2$: Calc.: C, 60.21; H, 5.37; Found: C, 60.29; H, 5.35.

Step D:
2-Cyclopentyl-2-methyl-5-methoxy-6,7-dichloro-1-indanone

2-Cyclopentyl-5-methoxy-6,7-dichloro-1-indanone (7.5 g., 0.025 mole) is dissolved in dry 1,2-dimethoxyethane (200 ml.) under nitrogen. Sodium hydride (57% in mineral oil; 1.16 g., 0.0275 mole) is then added and the mixture is stirred at 80° until evolution of hydrogen ceases (2 hours). The solution is cooled and methyl iodide (7.5 ml.) is added, the mixture is again brought to reflux and then cooled. Most of the 1,2-dimethoxyethane is evaporated and water is added to the residue which soon solidifies and is crystallized from methylcyclohexane and from ethanol-water (4:1) to obtain 3.4 g. of 2-cyclopentyl-2-methyl-5-methoxy-6,7-dichloro-1-indanone, m.p. 109°–111.5°C.

Elemental analysis for $C_{17}H_{18}Cl_2O_2$: Calc.: C, 61.35; H, 5.79; Found: C, 61.71; H, 5.84.

Step E:
2-Cyclopentyl-2-methyl-5-hydroxy-6,7-dichloro-1-indanone

2-Cyclopentyl-2-methyl-5-methoxy-6,7-dichloro-1-indanone (3.4 g., 0.0109 mole) is added to dry heptane (180 ml.) and aluminum chloride (4.36 g., 0.0327 mole) is added. The mixture is refluxed for one hour and the hexane is decanted from the gummy residue which then is added to ice water (200 ml.) containing 12N hydrochloric acid (15 ml.). The solid that separates is crystallized from benzene to obtain 2.77 g. of 2-cyclopentyl-2-methyl-5-hydroxy-6,7-dichloro-1-indanone, m.p. 190°–194°C.

Elemental analysis for $C_{16}H_{16}Cl_2O_2$: Calc.: C, 60.21; H, 5.37; Found: C, 60.43; H, 5.41.

Step F:
(1-Oxo-2-cyclopentyl-2-methyl-6,7-dichloro-5-indanyloxy)acetic Acid

2-Cyclopentyl-2-methyl-5-hydroxy-6,7-dichloro-1-indanone (2.77 g., 0.00926 mole) is added to dimethylformamide (DMF) (40 ml.). Potassium carbonate (3.21 g., 0.0232 mole) and ethyl bromoacetate (3.34 g., 0.0232 mole) are added. The mixture is stirred at 55°–60°C. for 2½ hours, then 40 ml. of 10% sodium hydroxide are added and the mixture is stirred at 80°–85°C. for 1½ hours. The mixture then is added to 500 ml. of 2% hydrochloric acid. The solid that separates is taken up in ether. The ether extract is washed with water, dried over magnesium sulfate and evaporated, leaving a gummy solid that is crystallized from acetic acid to obtain 950 mg. of (1-oxo-2-cyclopentyl-2-methyl-6,7-dichloro-5-indanyloxy)acetic acid which melts at 113°–114°C. (1-Oxo-2-cyclopentyl-2-methyl-6,7-dichloro-5-indanyloxy)acetic acid also has an allotropic form which melts at 139.5°–141°C.

Elemental analysis for $C_{17}H_{18}Cl_2O_4$: Calc.: C, 57.16; H, 5.08; Found: C, 57.29; H, 5.34

Step G:
(1-Hydroxyimino-2-cyclopentyl-2-methyl-6,7-dichloro-5-indanyloxy)acetic acid A stirred solution of (1-oxo-2-cyclopentyl-2-methyl-6,7-dichloro-5-indanyloxy)acetic acid (5.1 g., 0.015 mole) and hydroxyamine hydrochloride (3.2 g., 0.045 mole) in pyridine (60 ml.) is heated at 95°C. on a steam bath for 40 hours then poured into aqueous hydrochloric acid affording (1-hydroxyimino-2-cyclopentyl-2- methyl-6,7-dichloro-5-indanyloxy)acetic acid which melts at 230°C. after recrystallization from ethanol-water.

Elemental analysis for $C_{17}H_{19}Cl_2NO_4$: Calc.: C, 54.85; H, 5.14; N, 3.76; Found: C, 55.19; H, 5.17; N, 3.53.

EXAMPLE 2

[1'-Hydroxyimino-6',7'-dichlorospiro-(cyclopentane-1,2'-indan)-5'-yloxy]acetic acid

Step A: 2,3-Dichloro-4-(6-bromohexanoyl)-anisole

A stirred mixture of 2,3-dichloroanisole (89 g., 0.50 mole) and 6-bromohexanoylchloride (120 g., 0.59 mole) in methylene chloride (500 ml.) is cooled to 5°C. and treated with aluminum chloride (74 g., 0.56 mole) in portions during a one-half hour period. The reaction mixture is kept at 25°C. for 18 hours then poured into ice water (1 l.) containing hydrochloric acid (100 ml.) the organic phase is separated, washed with water, 2% sodium hydroxide and dilute hydrochloric acid. The methylene chloride is evaporated at reduced pressure. The crude product is dissolved in ether (200 ml.), dried over magnesium sulfate, filtered and treated with hexane (600 ml.) affording 2,3-dichloro-4-(6-bromohexanoyl)anisole which melts at 52°–53°C.

Elemental analysis for $C_{13}H_{15}BrCl_2O_2$: Calc.: C, 44.10; H, 4.27; Found: C, 44.33; H, 4.16.

Step B:
2-(4-Chlorobutyl)-5-methoxy-6,7-dichloro-1-indanone

A stirred mixture of 2,3-dichloro-4-(6-bromohexanoyl)anisole (10 g.), dimethylamine hydrochloride (4 g.), paraformaldehyde (2 g.) and acetic acid (0.5 ml.) is heated on a steam bath for 2 hours, treated with DMF (30 ml.) and heated an additional 2½ hours. The reaction mixture is poured into water, extracted with ether, washed with water and dried over magnesium sulfate. Evaporation of the ether affords 9 g. of crude 2,3-dichloro-4-(6-chloro-2-methylenehexanoyl)anisole which is cyclialkylated by treatment with concentrated sulfuric acid (50 ml.). The sulfuric acid solution is poured into water (300 ml.) affording 5.8 g. of 2-(4-chlorobutyl)-5-methoxy-6,7-dichloro-1-indanone which melts at 92°C. after recrystallization from cyclohexane.

Elemental analysis for $C_{14}H_{15}Cl_3O_2$: Calc.: C, 52.28; H, 4.70; Cl, 33.07; Found: C, 52.25; H, 4.50; Cl, 33.03.

Step C:
5'-Methoxy-6',7'-dichlorospiro-(cyclopentane-1,2'-indanone)

A stirred suspension of sodium hydride (370 mg., 0.0155 mole) in 1.2-dimethoxyethane (250 ml.) is refluxed in an inert atmosphere. A solution of 2-(4-chlorobutyl)-5-methoxy-6,7-dichloro-1-indanone (4.5 g., 0.014 mole) in 1,2-dimethoxyethane (50 ml.) is added over a 20-minute period and refluxing is maintained for 3 hours. The solvent is distilled to a volume of 50 ml. and poured into water (300 ml.) affording 2.6 g. of 5'-methoxy-6',7'-dichlorospiro(cyclopentane-1,2'-indanone) which melts at 170°C. after recrystallization from ethanol-water.

Elemental analysis for $C_{14}H_{14}Cl_2O_2$: Calc.: C, 58.97; H, 4.95; Found: C, 59.34; H, 5.08.

Step D:
5'-Hydroxy-6',7'-dichlorospiro-(cyclopentane-1,2'-indanone)

A stirred mixture of 5'-methoxy-6',7'-dichlorospiro(-cyclopentane-1,2'-indanone) (2.6 g., 0.0091 mole) and pyridine hydrochloride (26 g.) is heated at 185°C. for 1 hour, then poured into water (200 ml.). The 5'-hydroxy-6',7'-dichlorospiro-(cyclopentane-1,2'-indanone) which separates (2.3 g.) melts at 236°C. after recrystallization from nitromethane.

Elemental analysis for $C_{13}H_{12}Cl_2O_2$: Calc.: C, 57.55; H, 4.46; Found: C, 57.77; H, 4.54.

Step E:
[1'-Oxo-6',7'-dichlorospiro-(cyclopentane-1,2'-indan)-5'-yloxy]acetic acid

[1'-Oxo-6',7'-dichlorospiro-(cyclopentane-1,2'-indan)-5'-yloxy]acetic acid is prepared following substantially the same procedure described in Example 5, Step G, using the following substances: 5'-hydroxy-6',7'-dichlorospiro-(cyclopentane-1,2'-indanone) (2.3 g., 0.0085 mole), potassium carbonate (2.7 g.), ethyl bromoacetate (2.1 ml.) and DMF (25 ml.). The above procedure gives 2.7 g. (96%) of [1'-oxo-6',7'-dichlorospiro-(cyclopentane-1,2'-indan)-5'-yloxy]acetic acid which after recrystallization from nitromethane melts at 195°C.

Elemental analysis for $C_{15}H_{14}Cl_2O_4$: Calc.: C, 54.73; H, 4.29; Found: C, 55.00, H, 4.25.

Step F:
[1'-Hydroxyimino-6',7'-dichlorospiro-(cyclopentane-1,2'-indan)-5'-yloxy]acetic acid A stirred solution of (1'-oxo-6',7'-dichlorospiro-(cyclopentane-1,2'-indan-5'-yloxy)acetic acid (3.3 g., 0.01 mole) and hydroxylamine hydrochloride (2.1 g., 0.03 mole) in pyridine (50 ml.) is heated at 95°C. on a steam bath for 18 hours and poured into aqueous hydrochloric acid. The [1'-hydroxyimino-6',7'-dichlorospiro-(cyclopentane-1,2'-indan)-5'-yloxy]acetic acid which separates (2.2 g.) melts at 228°C. after recrystallization from acetonitrile.

Elemental analysis for $C_{15}H_{15}Cl_2NO_4$: Calc.: C, 52.34; H, 4.39; N, 4.07; Found: C, 52.37; H, 4.42; N, 4.17.

EXAMPLE 3

(1-Hydroxyimino-2-methyl-2-phenyl-6,7-dichloro-5-indanyloxy)acetic acid

Step A: 2',3'-Dichloro-4'-methoxyisobutyrophenone

A stirred mixture of 2,3-dichloroanisole (I) (100 g., 0.565 mole) and isobutyryl chloride (II) (66 g., 0.62 mole) in methylene chloride (400 ml.) is cooled to 5°C. and treated with aluminum chloride (83 g., 0.62 mole) during a 1 hour period. The reaction mixture is allowed to warm to 25°C. and after 24 hours is poured into ice water (400 ml.) and hydrochloric acid (30 ml.). The organic phase is washed with 5% sodium hydroxide, water, dried over magnesium sulfate and distilled at reduced pressure affording 68 g. of 2',3'-dichloro-4'-methoxyisobutyrophenone (III) which distills at 120°–130°C./0.5 mm.

Elemental analysis for $C_{11}H_{12}Cl_2O_2$: Calc.: C, 53,46; H, 4.89; Found: C, 54.25; H, 5.07.

Step B:
2-Bromo-2',3'-dichloro-4'-methoxyisobutyrophenone

A stirred solution of 2',3'-dichloro-4'-methoxyisobutyrophenone (45 g., 0.183 mole) in acetic acid (150 ml.) is treated during one-half hour with bromine (30 g., 0.187 mole). The reaction mixture is stirred 10 minutes, then poured into ice water (600 ml.) containing sodium bisulfite (2 g.). The 2-bromo-2',3'-dichloro-4'-methoxyisobutyrophenone (IV) which separate (48 g.) melts at 72°–73°C. after recrystallization from hexane.

Elemental analysis for $C_{11}H_{11}BrCl_2O_2$: Calc.: C, 40.52; H, 3.40; Found: C, 40.68; H, 3.38.

Step C:
2-Methylene-2',3'-dichloro-4'-methoxypropiophenone

A solution of 2-bromo-2',3'-dichloro-4'-methoxyisobutyrophenone (32 g., 0.1 mole) and anhydrous lithium bromide (17.4 g., 0.2 mole) in DMF (200 ml.) is stirred at 95°C. in an inert atmosphere for 3 hours and poured into ice water (500 ml.). The 2-methylene-2',3'-dichloro-4'-methoxypropiophenone (V) which separates melts at 59°C. after recrystallization from petroleum ether.

Elemental analysis for $C_{11}H_{10}Cl_2O_3$: Calc.: C, 53.90; H, 4.11; Found: C, 53.72; H, 4.11.

Step D: 2-Methyl-5-methoxy-6,7-dichloro-1-indanone

A solution of 2-methylene-2',3'-dichloro-4'-methoxypropiophenone (40 g., 0.163 mole) in concentrated sulfuric acid (75 ml.) is allowed to stand at 25°C. for 24 hours and then is slowly poured into vigorously stirred ice water (500 ml.). The 2-methyl-5-methoxy-6,7-dichloro-1-indanone (VI) which separate (40 mg.) melts at 129°C. after recrystallization from methylcyclohexane.

Elemental analysis for $C_{11}H_{10}Cl_2O_2$: Calc.: C, 53.90; H, 4.11; Found: C, 53.84; H, 4.00.

Step E:
2-Methyl-2-phenyl-5-methoxy-6,7-dichloro-1-indanone

Potassium tert-butoxide (8.42 g., 0.075 mole) dissolved in tert-butanol (300 ml.) is added to a refluxing solution of 2-methyl-5-methoxy-6,7-dichloro-1-indanone (12.26 g., 0.05 mole), refluxing is continued for 2 hrs., then a suspension of diphenyliodonium chloride (19.0 g., 0.06 mole) in tert-butanol (1 l.) is added and refluxing is continued for 2 hrs. The reaction mixture is cooled to 25°C., 300 ml. water added, and the mixture concentrated to dryness in vacuo to give 4.97 g. of 2-methyl-2-phenyl-5-methoxy-6,7-dichloro-1-indanone which melts at 161°–163°C. after crystallization from benzene:cyclohexane, 1:2.

Elemental analysis for $C_{17}H_{14}Cl_2O_2$: Calc.: C, 63.57; H, 4.39; Found: C, 63.24; H, 4.68.

Step F:
2-Methyl-2-phenyl-5-hydroxy-6,7-dichloro-1-indanone

A stirred mixture of 2-methyl-2-phenyl-5-methoxy-6,7-dichloro-1-indanone (4.94 g., 0.015 mole) and pyridine hydrochloride (50 g.) is heated at 175°C. for 1 hour, then poured into water (500 ml). The 2-methyl-2-phenyl-5-hydroxy-6,7-dichloro-1-indanone which separates (2.05 g.) melts at 194°–196°C. after recrystallization from ethanol: water, 2:1.

Elemental analysis for $C_{16}H_{12}Cl_2O_2$: Calc.: C, 62.56; H, 3.95; Found: C, 62.60; H, 4.11.

Step G:
(1-Oxo-2-methyl-2-phenyl-6,7-dichloro-5-indanyloxy)acetic acid

A stirred mixture of 2-methyl-2-phenyl-5-hydroxy-6,7-dichloro-1-indanone (2.05 g., 0.0067 mole), potassium carbonate (1.85 g., 0.0134 mole) and ethyl bromoacetate (2.23 g., 0.0134 mole) in dimethylformamide (30 ml.) is warmed at 55°–60°C. for 3 hours, then treated with potassium hydroxide (0.97 g., 0.0147 mole) dissolved in a minimum amount of water in methanol (30 ml.) and heated on a steam bath for 2½ hours. The reaction mixture is poured into water (500 ml.), acidified with 6 N hydrochloric acid and the precipitate collected after trituration with ether-petroleum ether and dried to give 1.31 g. of (1-oxo-2-methyl-2-phenyl-6,7-dichloro-5-indanyloxy)acetic acid which melts at 168°–169°C. on crystallization from acetic acid: water, 1:1.

Elemental analysis for $C_{18}H_{14}Cl_2O_4$: Calc.: C, 59.20; H, 3.86; Found: C, 58.94; H, 4.20.

Step H:
(1-Hydroximino-2-methyl-2-phenyl-6,7-dichloro-5-indanyloxy)acetic acid A stirred solution of (1-oxo-2-methyl-2-phenyl-6,7-dichloro-5-indanyloxy)acetic acid (5.48 g., 0.015 mole) and hydroxylamine hydrochloride (3.2 g., 0.045 mole) in pyridine (60 ml.) is heated at 95°C. on a steam bath for 36 hours then poured into aqueous hydrochloric acid affording (1-hydroximino-2-methyl-2-phenyl-6,7-dichloro-5-indanyloxy)acetic acid.

EXAMPLE 4

Preparation of
[1-Hydroximino-2-(4-chlorophenyl)-2-methyl-6,7-dichloro-5-indanyloxy]acetic acid

Step A:
2-(4-Chlorophenyl-2-methyl-5-methoxy-6,7-dichloro-1-indanone

Potassium tert-butoxide (2.81 g., 0.025 mole) dissolved in tert-butanol (150 ml.) is added to a refluxing solution of 2-methyl-5-methoxy-6,7-dichloro-1-indanone (4.90 g., 0.02 mole) in tert-butanol (100 ml.)-benzene (200 ml.) refluxing is continued for 3 hours, then 4,4'-dichlorodiphenyliodonium chloride (11.55 g., 0.03 mole) is added and refluxing is continued for 2 hours. The reaction mixture is cooled to 25°C., 100 ml. water added, and the mixture concentrated to dryness in vacuo to give 4.30 g. of 2-(4-chlorophenyl-2-methyl-5-methoxy-6,7-dichloro-1-inandone which melts at 176°–178.5°C. after crystallization from cyclohexane:benzene, 5:1.

Step B:
2-(4-chlorophenyl)-2-methyl-5-hydroxy-6,7-dichloro-1-indanone

A stirred mixture of 2-(4-chlorophenyl)-2-methyl-5-methoxy-6,7-dichloro-1-indanone (4.15 g., 0.012 mole) and pyridine hydrochloride (40 g.) is heated at 180°C. for 1 hour, then poured into water (500 ml.). The 2-(4-chlorophenyl)-2-methyl-5-hydroxy-6,7-dichloro-1-indanone which separates (3.11 g.) melts at 211°–213°C. after crystallization from ethanol:water, 1:1.

Elemental analysis for $C_{16}H_{11}Cl_3O_2$: Calc.: C, 56.25; H, 3.25; Found: C, 55.53; H, 3.23.

Step C:
[1-Oxo-2-(4-chlorophenyl)-2-methyl-6,7-dichloro-5-indanyloxy]acetic acid hemihydrate A stirred mixture of 2-(4-chlorophenyl)-2-methyl-5-hydroxy-6,7-dichloro-1-indanone (2.95 g., 0.00863 mole), potassium carbonate (2.26 g., 0.0163 mole) and ethylbromoacetate (2.72 g., 0.0163 mole) in dimethylformamide (50 ml.) is warmed at 55°–60°C. for 2 hours, then treated with water (50 ml.)-10N sodium hydroxide solution (2.5 ml., 0.025 mole) and heated at 80°C. for 1 hour. The reaction mixture is added slowly to water (500 ml.)-12N hydrochloric acid (10 ml.) to precipitate 1.37 g. of [1-oxo-2-(4-chlorophenyl)-2-methyl-6,7-dichloro-5-indanyloxy]acetic acid hemihydrate which melts at 141°–142.5°C. after crystallization from acetic acid: water, 1:1.

Elemental analysis for $C_{18}H_{13}Cl_3O_4 \cdot 1/2H_2O$: Calc.: C, 52.90; H, 3.45; Cl, 26.03; Found: C, 52.47; H, 3.45; Cl, 26.11.

Step D:
[1-Hydroximino-2-(4-chlorophenyl)-2-methyl-6,7-dichloro-5-indanyloxy]acetic acid A stirred solution of [1-oxo-2-(4-chlorophenyl)-2-methyl-6,7-dichloro-5-indanyloxy]acetic acid hemihydrate (6.12 g., 0.015 mole) and hydroxylamine hydrochloride (3.2 g., 0.045 mole) in pyridine (60 ml.) is heated at 95°C. on a steam bath for 36 hours then poured into aqueous hydrochloric acid affording [1-hydroximino-2-(4-chlorophenyl)-2-methyl-6,7-dichloro-5-indanyloxy]acetic acid.

EXAMPLE 5

5-(1-Hydroximino-2-isopropyl-2-methyl-6,7-dichloro-5-indanyloxy-methyl)-tetrazole Step A: 2′,3′-Dichloro-4′-methoxyisovalerophenone A stirred mixture of 2,3-dichloroanisole (265 g., 1.50 mole) and isovaleryl chloride (200 g., 1.64 mole) in methylene chloride (1.2 l.) is cooled to 5°C. and treated with aluminum chloride (200 g., 1.64 mole) during a 2 hour period. The reaction is allowed to warm to 25°C. and after 24 hours is poured into ice water (3 l.) and hydrochloric acid (600 ml.). The organic phase is washed with 10% sodium hydroxide and water and dried over magnesium sulfate. After evaporation of the solvent, the product is crystallized from hexane affording 295 g. of 2′,3′-dichloro-4′-methoxyisovalerophenone which melts at 49°–54°C.

Elemental analysis for $C_{12}H_{14}Cl_2O_2$: Calc.: C, 55.19; H, 5.40; Found: C, 55.38; H, 5.51.

Step B:
2-Methylene-2′,3′-dichloro-4′-methoxyisovalerophenone

A stirred mixture of 2′,3′-dichloro-4′-methoxyisovalerophenone (261.6 g., 1.0 mole), paraformaldehyde (75.0 g., 2.5 mole), dimethylamine hydrochloride (327 g., 4.0 mole) and acetic acid (26 ml.) is heated on a steam bath for 18 hours, treated with DMF (500 ml.), heated an additional 3 hours, then poured into ice water (1.7 l.). The crude product which separates is dissolved in benzene (600 ml.) and dried over sodium sulfate. Evaporation of the benzene affords 237 g. of 2-methylene-2′,3′-dichloro-4′-methoxyisovalerophenone which melts at 46°–51°C. and is used in Step C without further purification.

Step C:
2-isopropyl-5-methoxy-6,7-dichloro-1-indanone

A solution of the product of Step B (237 g.) in concentrated sulfuric acid (400 ml.) is stirred at 25°C for 2 hours, then slowly added to a copious amount of ice water. The product which separates is triturated with fresh water, neutralized with aqueous sodium bicarbonate, filtered and dried. Recrystallization from benzene-hexane affords 134 g. of 2-isopropyl-5-methoxy-6,7-dichloro-1-indanone which melts at 118°–119°C.

Elemental analysis for $C_{13}H_{14}Cl_2O_2$: Calc. C, 57.16; H, 5.17; Found: C, 57.23; H, 5.33.

Step D:
2-Methyl-2-isopropyl-5-methoxy-6,7-dichloro-1-indanone

A stirred suspension of 2-isopropyl-5-methoxy-6,7-dichloro-1-indanone (7.3 g., 0.025 mole) and sodium hydride (810 mg., 0.028 mole) in anhydrous 1,2-dimethoxyethane (250 ml.) is heated in an inert atmosphere at 80°–85°C. for 1 hour, cooled to 30°C. and treated with methyl iodide (6 ml.). The reaction mixture is heated to 80°C. then the solvent is distilled at reduced pressure and the residue poured into ice water. The 2-methyl-2-isopropyl-5-methoxy-6,7-dichloro-1-indanone which separates (7.0 g.) melts at 143°C. after recrystallization from ethanol-water.

Elemental analysis for $C_{14}H_{16}Cl_2O_2$: Calc.: C, 58.55; H, 5.62; Found: C, 58.82; H, 5.60.

Step E:
2-Methyl-2-isopropyl-5-hydroxy-6,7-dichloro-1-indanone

A stirred suspension of 2-methyl-2-isopropyl-5-methoxy-6,7-dichloro-1-indanone (7.0 g., 0.0244 mole) and aluminum chloride (9.0 g., 0.068 mole) in heptane (400 ml.) is refluxed for 1 hour and cooled. The heptane is decanted from the reaction mixture and the solid residue is poured into water (300 ml.) and concentrated hydrochloric acid (20 ml.). The crude product is extracted into ether (300 ml.), washed with water, dried over magnesium sulfate, distilled to a volume of 100 ml. and treated with hexane (100 ml.). The 2-methyl-2-isopropyl-5-hydroxy-6,7-dichloro-1-indanone which separates (6.5 g.) melts at 215°C.

Elemental analysis for $C_{13}H_{14}Cl_2O_2$: Calc.: C, 57.16; H, 5.17; Found: C, 56.90; H, 5.15.

Step F:
(1-Oxo-2-isopropyl-2-methyl-6,7-dichloro-5-indanyloxy)acetonitrile

A stirred mixture of 2-isopropyl-2-methyl-5-hydroxy-6,7-dichloro-1-indanone (8.2 g., 0.03 mole), potassium carbonate (4.15 g., 0.03 mole), chloroacetonitrile (2.4 g., 0.032 mole) and potassium iodide (0.5 g.) in acetone is refluxed for 18 hours. The solvent is evaporated and the residue is treated with water (100 ml.) affording 8.0 g. of (1-oxo-2-isopropyl-2-methyl-6,7-dichloro-5-indanyloxy) acetonitrile which melts at 133°C. After recrystallization from butyl chloride.

Elemental analysis for $C_{15}H_{15}Cl_2NO_2$: Calc.: C, 57.71; H, 4.84; N, 4.49; Found: C, 57.53; H, 4.72; N, 4.57.

Step G:
5-(1-Oxo-2-isopropyl-2-methyl-6,7-dichloro-5-indanyloxymethyl)tetrazole A stirred solution of (1-oxo-2-isopropyl-2-methyl-6,7-dichloro-5-indanyloxy)acetonitrile (6.2 g., 0.02 mole), sodium azide (1.55 g., 0.024 mole) and ammonium chloride (1.24 g., 0.023 mole) in DMF (30 ml.) is heated in an inert atmosphere for 1 hour, poured into water (200 ml.) and acidified with hydrochloric acid. The 5-(1-oxo-2-isopropyl-2-methyl-6,7-dichloro-5-indanyloxymethyl) tetrazole which separates (4.2 g.) melts at 173°C. after recrystallization from methanol-water.

Elemental analysis for $C_{15}H_{16}Cl_2N_4O_2$: Calc.: C, 50.72; H, 4.54; N, 15.77; Found: C, 50.53; H, 4.36; N, 15.66.

Step H:
5-(1-Hydroximino-2-isopropy-2-methyl-6,7-dichloro-5-indanyloxymethyl)tetrazole A stirred solution of (1-oxo-2-isopropy-2-methyl-6,7-dichloro-5-indanyloxymethyl)tetrazole (5.0 g., 0.015 mole) in pyridine (60 ml.) is heated at 95°C. on a steam bath for 40 hours then poured into aqueous hydrochloric acid affording 5-(1-hydroximino-2-isopropyl-2-methyl-6,7-dichloro-5-indanyloxymethyl)tetrazole.

EXAMPLE 6
5-(1-Hydroximino-2-cyclopentyl-2-methyl-6,7-dichloro-5-indanyloxymethyl)tetrazole

Step A:
(1-Oxo-2-cyclopentyl-2-methyl-6,7-dichloro-5-indanyloxy)acetonitrile By following substantially the same procedure described in Example 5, Step F, using the following substances: 2-cyclopentyl-2-methyl-5-hydroxy-6,7-dichloro-1-indanone (8.98 g., 0.03 mole), potassium carbonate (4.15 g.), chloroacetonitrile (2.26 g., 0.03 mole), potassium iodide (0.495 g.) and acetone (150 ml.) there is obtained 7.40 g. (73%) of (1-oxo-2-cyclopentyl-2-methyl-6,7-dichloro-5-indanyloxy)acetonitrile which after recrystallization from benzenecyclohexane (1:10) melts at 130°–131°C.

Elemental analysis for $C_{17}H_{17}Cl_2NO_2$: Calc.: C, 60.36; H, 5.07; N, 4.14; Found: C, 60.62; H, 5.08; N, 3.88.

Step B:
5-(1-Oxo-2-cyclopentyl-2-methyl-6,7-dichloro-5-indanyloxymethyl)tetrazole By following substantially the same procedure described in Example 5, Step G, using the following substances: (1-oxo-2-cyclopentyl-2-methyl-6,7-dichloro-5-indanyloxy)-acetonitrile (7.20 g., 0.0213 mole), dimethylformamide (40 ml.), sodium azide (1.69 g., 0.0259 mole) and ammonium chloride (1.39 g., 0.0259 mole) there is obtained 4.74 g. of 5-(1-oxo-2-cyclopentyl-2-methyl-6,7-dichloro-5-indanyloxymethyl)tetrazole which melts at 218°–219°C. after recrystallization from ethanol.

Elemental analysis for $C_{17}H_{18}Cl_2N_4O_2$: Calc.: C, 53.55; H, 4.76; N, 14.70; Found: C, 53.63; H, 4.88; N, 14.77.

Step C:
5-(1-Hydroxyimino-2-cyclopentyl-2-methyl-6,7-dichloro-5-indanyloxymethyl)-tetrazole A stirred solution of (1-oxo-2-cyclopentyl-2-methyl-6,7-dichloro-5-indanyloxymethyl)tetrazole (5.7 g., 0.015 mole) and hydroxylamine hydrochloride (3.2 g., 0.045 mole) in pyridine (60 ml.) is heated at 95°C. on a steam bath for 30 hours then poured into aqueous hydrochloric acid affording 5-(1-hydroximino-2-cyclopentyl-2-methyl-6,7-dichloro-5-indanyloxymethyl)tetrazole.

EXAMPLE 7
5-[1'Hydroximino-6',7'dichlorospiro((cyclopentane-1,2'-indan)-5'-yloxymethyl]tetrazole

Step A:
[1'-Oxo-6',7'-dichlorospiro(cyclopentane-1,2'-indan)-5'-yloxy]acetonitrile The title compound is prepared following substantially the same procedure described in Example 5, Step F, using the following substances: 5'-hydroxy-6',7'-dichlorospiro(cyclopentane-1,2'-indanone) (8.4 g.), potassium carbonate (4.15 g.), chloroacetonitrile (2.4 g.), potassium iodide (0.5 g.) and acetone (150 ml.). This procedure affords 9.0 g. of [1'-oxo-6',7'-dichlorospiro(cyclopentane-1,2'-indan)-5'-yloxy]acetonitrile which after recrystallization from butyl chloride melts at 153°C.

Elemental analysis for $C_{15}H_{13}Cl_2NO_2$: Calc.: C, 58.08; H, 4.22; N, 4.52; Found: C, 58.27; H, 4.22; N, 4.35.

Step B:
5-[1'-Oxo-6',7'-dichlorospiro(cyclopentane-1,2'-indan)-5'-yloxymethyl]tetrazole The title compound is prepared following substantially the same procedure described in Example 5, Step G, using the following substances: [1'-oxo-6',7'-dichlorospiro(cyclopentane-1,2'-indan)-5'-yloxy]acetonitrile (5.3 g.), sodium azide (1.44 g.), ammonium chloride (1.14 g.) and dimethylformamide (35 ml.). This procedure affords 5.0 g. (83%) of 5-[1'-oxo-6',7'-dichlorospiro(cyclopentane-1,2'-indan)5'-yloxymethyl]tetrazole which after recrystallization from acetonitrile melts at 191°C.

Elemental analysis for $C_{15}H_{14}Cl_2N_4O_2$: Calc.: C, 51.01; H, 3.99; N, 15.86; Found: C, 51.27; H, 3.99; N, 16.22.

Step C:
5-[1'-Hydroximino-6',7'-dichlorospiro-(cyclopentane-1,2'-indan)-5'-yloxymethyl]tetrazole A stirred solution of (1-oxo-2-methyl-2-phenyl-6,7-dichloro-5-indanyloxy)acetic acid (5.3 g., 0.015 mole) and hydroxylamine hydrochloride (3.2 g., 0.045 mole) in pyridine (60 ml.) is heated at 95°C. on a steam bath for 30 hours then poured into aqueous hydrochloric acid affording 5-[1'-Hydroximino-6',7'-dichlorospiro(-cyclopentane-1,2'-indan)-5'-yloxymethyl]tetrazole.

EXAMPLES 8 – 35

Following the procedure exactly as described in Example 1, Step G, except that there is substituted for the (1-oxo-2-cyclopentyl-2-methyl-6,7-dichloro-5-indanyloxy) acetic acid an equivalent amount of a [1- oxo-2,2-disubstituted indanyl (or thio)] alkanoic acid having the structure:

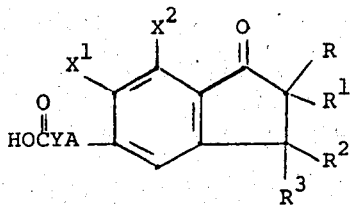

I there is obtained the corresponding 1-hydroximino compounds of the present invention, having the structure:

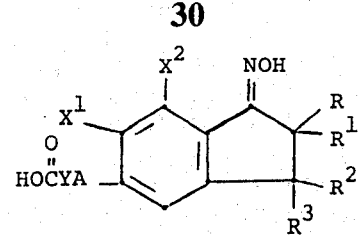

The [1-oxo-2,2-disubstituted indanyl (or thio)] alkanoic acids (formula I, above) are fully disclosed in commonly assigned, co-pending applications Ser. Nos. 399,571 and 399,568, both filed Sept. 21, 1973 (Merck & Co., Inc. Attorney's Docket Numbers 15574 and 15584) which applications are entitled 1-Oxo-2,2-Disubstituted-5-Indanyloxy (or thio) Alkanoic Acids and [1-Oxo-2,3-Hydrocarbylene-5-Indanyloxy (or thio)]Alkanoic Acids, respectively) which, applications are incorporated herein by reference.

Table I summarizes the resulting compounds of Examples 8 – 35.

Table I

| Ex. No. | A | Y | R | $R^1$ | $R^2$ | $R^3$ | $X^1$ | $X^2$ |
|---|---|---|---|---|---|---|---|---|
| 8 | O | $CH_2$ | $CH_3$ | ---$(CH_2)$--- | | H | Cl | Cl |
| 9 | O | $CH_2$ | $C_2H_5$ | —$CH_2OH$ | H | H | Cl | Cl |
| 10 | O | $CH_2$ | $CH(CH_3)_2$ | —$CH_2OH$ | H | H | Cl | Cl |
| 11 | O | $CH_2$ | $CH_3$ | $C_2H_5$ | H | H | Cl | Cl |
| 12 | O | $CH_2$ | $CH_3$ | $CH_3$ | H | H | Cl | Cl |
| 13 | O | $CH_2$ | $C_2H_5$ | $CH_2CH_2CH_3$ | H | H | Cl | Cl |
| 14 | O | $CH_2$ | $CH_3$ | $CH_2CH=CH_2$ | H | H | Cl | Cl |
| 15 | O | $CH_2$ | $C_2H_5$ | $C_2H_5$ | H | H | Cl | Cl |
| 16 | O | $CH_2$ | $CH_3$ | $CH(CH_3)_2$ | H | H | Cl | Cl |
| 17 | O | $CH_2$ | $CH_3$ | —$CH_2$—Ph | H | H | Cl | Cl |
| 18 | O | $CH_2$ | | ---$(CH_2)_5$--- | H | H | Cl | Cl |
| 19 | O | $CH_2$ | $CH_3$ | cyclopropyl | H | H | $CH_3$ | Cl |
| 20 | O | $CH_2$ | $CH_3$ | $CH_2CH=CH$—Ph | H | H | Cl | Cl |
| 21 | O | $CH_2$ | $CH_3$ | $CH_3$ | $CH_3$ | H | Cl | Cl |
| 22 | O | $CH_2$ | $CH_3$ | $CH_3$ | H | H | $CH_3$ | $CH_3$ |
| 23 | O | $-C(CH_3)_2-$ | $CH_3$ | cyclopropyl | H | H | Cl | Cl |
| 24 | O | $(CH_2)_4$ | $CH_3$ | cyclopropyl | H | H | Cl | Cl |
| 25 | O | $(CH_2)_3$ | $CH_3$ | cyclopropyl | H | H | Cl | Cl |
| 26 | S | $CH_2$ | $CH_3$ | cyclopropyl | H | H | Cl | Cl |
| 27 | O | $CH_2$ | $CH_3$ | $CH_3$ | Ph | H | Cl | Cl |
| 28 | O | $CH_2$ | $CH_3$ | $CH_3$ | Ph | $CH_3$ | Cl | Cl |
| 29 | O | $CH_2$ | $CH(CH_3)_2$ | $CH_2CH_2CHOHCH_3$ | H | H | Cl | Cl |
| 30 | O | $CH_2$ | $CH_3$ | cyclopentyl-OH | H | H | Cl | Cl |
| 31 | O | $CH_2$ | $CH_3$ | $C_2H_5$ | Ph | H | Cl | Cl |
| 32 | O | $CH_2$ | $CH(CH_3)_2$ | $CH_2OC(CH_3)_3$ | H | H | Cl | Cl |
| 33 | O | $CH_2$ | $C_2H_5$ | -----$CH_2$----- | | H | Cl | Cl |
| 34 | O | $CH_2$ | $CH(CH_3)_2$ | -----$CH_2$----- | | H | Cl | Cl |
| 35 | O | $CH_2$ | $CH_3$ | ----$(CH_2)_4$--- | | H | Cl | Cl |

The novel compounds of this invention are diuretic and saluretic agents. In addition, these compounds are also able to maintain the uric acid concentration in the blood at pretreatment levels or even cause a decrease in uric acid concentration.

Also the compounds of this invention are antihypertensive agents. Generally, we have found that an aryl or substituted aryl group but particularly a phenyl group at the 3-position of the compounds of Formula I will increase the uricosuric activity of the compounds when compared to the diuretic or saluretic activities.

The compounds of this invention can be administered in a wide variety of therapeutic dosages in conventional vehicles as, for example, by oral administration in the form of a tablet or by intravenous injection. Also, the daily dosage of the products may be varied over a wide range as, for example, in the form of scored tablets containing 5, 10, 25, 50, 100, 150, 250 and 500 milligrams of the active ingredient for the symptomatic adjustment of the dosage to the patient to be treated. These dosages are well below the toxic or lethal dose of the products.

A suitable unit dosage form of the products of this invention can be administered by mixing 50 milligrams of a 1-hydroxyimino-2,2-disubstituted-5-indanyloxyalkanoic acid (I) or a suitable salt, ester or amide derivative thereof, with 149 mg. of lactose and 1 mg. of magnesium stearate and placing the 200 mg. mixture into a No. 1 gelatin capsule. Similarly, by employing more of the active ingredient and less lactose, other dosage forms can be put up in No. 1 gelatin capsules and should it be necessary to mix more than 200 mg. of ingredients together, larger capsules may be employed. Compressed tablets, pills, or other desired unit dosages can be prepared to incorporate the compounds of this invention by conventional methods, and if desired, can be made up as elixirs or as injectable solutions by methods will known to pharmacists. An effective amount of the drug is ordinarily supplied at a dosage level of from about 0.1 mg. to about 50 mg./kg. of body weight. Preferably the range is from about 1 mg. to 7 mg./kg. of body weight.

It is also within the scope of this invention to combine two or more of the compounds of this invention in a unit dosage form or to combine one or more of the compounds of this invention with other known diuretics and saluretics or with other desired therapeutic and/or nutritive agents in dosage unit form. For example, the compounds of this invention can be combined with anticalureticdiuretic or with anti-hypertensive compounds, and particularly with an agent such as reserpine. Also a combination or mixture of different indanones of Formula I with each other can be advantageous particularly where one compound has greater diuretic activity and the other has greater uricosuric activity.

The following example is included to illustrate the preparation of a representative dosage form:

EXAMPLE 36

Dry-filled capsules containing 50 mg. of active ingredient per capsule

| | Per Capsule |
|---|---|
| (1-Hydroxyimino-2-cyclopentyl-2-methyl-6,7-dichloro-5-indanyloxy)acetic acid | 50 mg. |
| Lactose | 149 mg. |
| Magnesium Stearate | 1 mg. |
| Capsule (Size No. 1) | 200 mg. |

The (1-hydroxyimino-2-cyclopentyl-2-methyl-6,7-dichloro-5-indanyloxy)acetic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other novel compounds of this invention.

EXAMPLE 37

Parenteral Solution of Sodium (1-hydroxyimino-2-cyclopentyl-2-methyl-6,7-dichloro-5-indanyloxy)acetate 100 Mg. of (1-hydroxyimino-2-cyclopentyl-2-methyl-6,7-dichloro-5-indanyloxy)acetic acid are dissolved in 3 ml. of 0.1 N-sodium hydrogen carbonate solution. The solution is made up to 10 ml. with water and sterilized.

EXAMPLE 38

Dry-filled capsule containing 50 mg. of active ingredient and 5 mg. of N-amidino-(3,5-diamino-6-chloropyrazine)-2-carboxamide per capsule

| | Per Capsule |
|---|---|
| (1-Hydroxyimino-2-cyclopentyl-2-methyl-6,7-dichloro-5-indanyloxy)acetic acid | 50 mg. |
| N-amidino-(3,5-diamino-6-chloro-pyrazine)-2-carboxamide | 5 mg. |
| Lactose | 144 mg. |
| Magnesium stearate | 1 mg. |
| Capsule (size No. 1) | 200 mg. |

The (1-hydroxyimino-2-cyclopentyl-2-methyl-6,7-dichloro-5-indanyloxy)acetic acid and N-amidino-(3,5-diamino-6-chloropyrazine)-2-carboxamide are united and reduced to a No. 60 powder and then lactose and magnesium stearate are passed through a No. 60 bolting cloth onto the powder and the combined ingredients admixed for ten minutes and then filled into a No. 1 dry gelatin capsule.

EXAMPLE 39

Dry-filled capsules containing 50 mg. of active ingredient and 0.125 mg. of reserpine per capsule

| | Per Capsule |
|---|---|
| 1-Hydroxyimino-2-cyclopentyl-2-methyl-6,7-dichloro-5-indanyloxy)acetic acid | 50 mg. |
| Reserpine | 0.125 mg. |
| Lactose | 148.875 mg. |
| Magnesium stearate | 1 mg. |
| Capsule (size No. 1) | 200 mg. |

The (1-hydroxyimino-2-cyclopentyl-2-methyl-6,7-dichloro-5-indanyloxy)acetic acid and reserpine are united and reduced to a No. 60 powder and then lactose and magnesium stearate are passed through a No. 60 bolting cloth onto the powder and the combined ingredients are admixed for ten minutes and then filled into a No. 1 dry gelatin capsule.

Similar dry-filled capsules can be prepared by replacing the indanyloxyacetic acid ingredient of the above example by any of the compounds of this invention.

EXAMPLE 40

Dry-filled capsules containing 25 mg. of active ingredient and 250 mg. of levo-3-(3,4-dihydroxyphenyl)-2-methylalanine

|  | Per Capsule |
|---|---|
| 1-Hydroximino-2-cyclopentyl-2-methyl-6,7-dichloro-5-indanyloxy)acetic acid | 25 mg. |
| Levo-3-(3,4-dihydroxyphenyl)-2-methylalanine | 250 mg. |
| Lactose | 124 mg. |
| Magnesium Stearate | 1 mg. |
| Capsule (Size No. 0) | 400 mg. |

The (1-hydroximino-2-cyclopentyl-2-methyl-6,7-dichloro-5-indanyloxy)acetic acid and levo-3-(3,4-dihydroxyphenyl)-2-alanine are united and reduced to a No. 60 powder and then lactose and magnesium stearate are passed through a No. 60 bolting cloth onto the powder and the combined ingredients admixed for 10 minutes and then filled into a No. 0 dry gelatin capsule.

It will be apparent from the foregoing description that the 1-hydroximino-2,2-disbustituted-5-indanyloxyalkanoic acid products (I) of this invention constitute a valuable class of compounds which have not been prepared heretofore. Once skilled in the art will also appreciate that the processes disclosed in the above examples are merely illustrative and are capable of a wide variation and modification without departing from the spirit of this invention.

What is claimed is:

1. A compound of the formula:

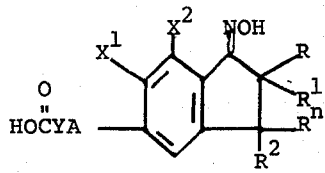

wherein
A is oxygen or sulphur;
R is lower alkyl, cycloalkyl having from 3 to 6 carbon atoms, phenyl, or halo-, hydroxy-, lower alkoxy-, nitro or lower alkyl-substituted phenyl;
$R^1$ is lower alkyl, lower alkenyl having from 3 to 5 carbon atoms, lower alkynyl, containing from 3 to 5 carbon atoms, phenyl lower alkyl, phenyl lower alkenyl, hydroxy lower alkyl, lower alkoxy lower alkyl, oxo lower alkyl, hydroxy cycloalkyl having from 4 to 6 carbon atoms and cycloalkyl lower alkyl having 4 to 7 carbon atoms;
R and $R^1$ may be joined together with the carbon atom to which they are attached to form a cycloalkyl radical containing from 3 to 7 nuclear carbon atoms, or a hydroxy, or lower alkyl substituted cycloalkyl radical having from 3 to 7 nuclear carbon atoms;
$R^2$ is hydrogen, lower alkyl, phenyl, or lower alkyl substituted phenyl;
$R^n$ is hydrogen, or methyl;
$R^1$ and $R^2$ may be joined together to form a hydrocarbylene ring having up to 5 carbon atoms;
$X^1$ is hydrogen, methyl or halo; and
$X^2$ is methyl or halo; or
$X^1$ and $X^2$ may be joined to form a hydrocarbylene chain containing 3 to 4 carbon atoms; and
Y is alkylene or haloalkylene containing from 1 to about 4 carbon atoms, and the non-toxic pharmacologically acceptable salt derivatives thereof.

2. A compound of the formula:

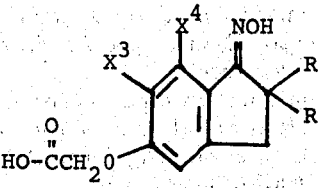

wherein
$R^3$ is phenyl or halo, hydroxy, lower alkyl or lower alkoxy substituted phenyl, lower alkyl having from 1 to 3 carbon atoms, cycloalkyl containing 5 or 6 carbon atoms, hydroxy cycloalkyl containing 4 to 6 carbon atoms, or phenyl lower alkyl;
$R^4$ is lower alkyl having from 1 to 3 carbon atoms;
$R^3$ and $R^4$ may be joined together with the carbon atom to which they are attached to form a cycloalkyl containing 5 to 6 carbon atoms;
$X^3$ and $X^4$ are the same or different radicals selected from methyl or chloro;
and the non-toxic, pharmacologically acceptable salt, derivatives thereof.

3. A compound according to claim 2 wherein $R^3$ is cyclopentyl; $R^4$ is methyl and $X^3$ and $X^4$ are chloro which is (1-hydroximino-2-methyl-2-cyclopentyl-6,7-dichloro-5-indanyloxy)acetic acid.

4. The sodium salt of the compound of claim 3.

5. A compound according to claim 2 wherein $R^3$ is isopropyl; $R^4$ is methyl and $X^3$ and $X^4$ are chloro which is (1-hydroximino-2-methyl-2-isopropyl-6,7-dichloro-5-indanyloxy)acetic acid.

6. A compound according to claim 2 wherein $R^3$ is benzyl; $R^4$ is methyl and $X^3$ and $X^4$ are chloro; which is (1-hydroximino-2-benzyl-2-methyl-6,7-dichloro-5-indanyloxy)acetic acid.

7. A compound according to claim 2 wherein $R^3$ is ethyl; $R^4$ is methyl and $X^3$ and $X^4$ are chloro; which is (1-hydroximino-2-ethyl-2-methyl-6,7-dichloro-5-indanyloxy)acetic acid.

8. A compound according to claim 2 wherein $R^4$ is methyl; $R^3$ is phenyl; and $X^3$ and $X^4$ are chloro; which is (1-hydroximino-2-methyl-2-phenyl-6,7-dichloro-5-indanyloxy)acetic acid.

9. A compound according to claim 2 wherein $R^3$ and $R^4$ are joined to form a cyclopentane ring and $X^3$ and $X^4$ are chloro; which is [1'-hydroximino-6',7'-dichlorospiro(cyclopentane-1,2'-indan)-5'-yloxy]acetic acid.

10. A compound according to claim 2 wherein $R^3$ and $R^4$ are joined together with the carbon atom to which they are attached to form cyclohexane ring and $X^3$ and $X^4$ are chloro; which is [1'-hydroximino-6',7'-dichlorospiro(cyclohexane-1,2'-indan)-5'-yloxy]acetic acid.

11. A compound according to claim 2 wherein $R^3$ is hydroxy cyclopentyl; $R^4$ is methyl and $X^3$ and $X^4$ are chloro; which is (1-hydroximino-2-hydroxy-cyclopentyl-2-methyl-6,7-dichloro-5-indanyloxy)acetic acid.

12. A compound according to claim 2 wherein $R^4$ is isopropyl; $R^3$ is hydroxymethyl; and $X^3$ and $X^4$ are chloro; which is (1-hydroximino-2-hydroxymethyl-2-isopropyl-6,7-dichloro-5-indanyloxy)acetic acid.

13. A compound according to claim 2 wherein $R^4$ is isopropyl; $R^3$ is t-butoxymethyl and $X^3$ and $X^4$ are chloro; which is (1-hydroximino-2-isopropyl-2-tert-butoxymethyl)-6,7-dichloro-5-indanyloxy)acetic acid.

14. A compound according to claim 2 wherein $R^3$ and $R^4$ are methyl and $X^3$ and $X^4$ are chloro; which is (1-hydroximino-2,2-dimethyl-6,7-dichloro-5-indanyloxy)acetic acid.

15. A compound according to claim 2 wherein $R^3$ is cyclopentyl; $R^4$ is methyl; $X^3$ is methyl and $X^4$ is chloro; which is (1-hydroximino-2-cyclopentyl-2,6-dimethyl-7-chloro-5-indanyloxy)acetic acid.

16. A compound according to claim 1 wherein R and $R^1$ taken together are propylene; $X^1$ and $X^2$ are chloro; A is oxygen and $R^n$ and $R^2$ are hydrogen which is [1'-hydroximino-2-methyl-6',7'-dichlorospiro(cyclopropane-1,2'-indan)-5'-yloxy]acetic acid.

17. A compound according to claim 1 wherein R, $R^1$ and $R^n$ are methyl; $R^2$ is phenyl; A is oxygen; Y is methylene and $X^1$ and $X^2$ are chloro; which is (1-hydroximino-2,2,3-trimethyl-3-phenyl-6,7-dichloro-5-indanyloxy)acetic acid.

18. A compound according to claim 1 wherein R is methyl; $R^1$ is ethyl; $R^2$ is phenyl; $R^n$ is hydrogen; A is oxygen; Y is methylene and $X^1$ and $X^2$ are chloro; which is (1-hydroximino-2-ethyl-2-methyl-3-phenyl-6,7-dichloro-5-indanyloxy)acetic acid.

* * * * *